(12) United States Patent
Sansone et al.

(10) Patent No.: US 10,137,287 B2
(45) Date of Patent: Nov. 27, 2018

(54) DRUG DELIVERY DEVICES AND METHODS FOR CONTROLLED DRUG RELEASE THROUGH DEVICE ORIFICE

(71) Applicant: TARIS Biomedical LLC, Lexington, MA (US)

(72) Inventors: Matthew Sansone, Dracut, MA (US); Karen Daniel, Newton, MA (US); Grace Kim, Cambridge, MA (US); Heejin Lee, Bedford, MA (US)

(73) Assignee: TARIS Biomedical LLC, Lexington, MA (US)

( * ) Notice: Subject to any disclaimer, the term of this patent is extended or adjusted under 35 U.S.C. 154(b) by 532 days.

(21) Appl. No.: 14/768,291

(22) PCT Filed: Mar. 5, 2014

(86) PCT No.: PCT/US2014/020703
§ 371 (c)(1),
(2) Date: Aug. 17, 2015

(87) PCT Pub. No.: WO2014/138214
PCT Pub. Date: Sep. 12, 2014

(65) Prior Publication Data
US 2015/0360012 A1   Dec. 17, 2015

Related U.S. Application Data

(60) Provisional application No. 61/772,751, filed on Mar. 5, 2013.

(51) Int. Cl.
*A61M 31/00*   (2006.01)
*A61K 9/00*   (2006.01)
*A61M 37/00*   (2006.01)

(52) U.S. Cl.
CPC ......... *A61M 31/002* (2013.01); *A61K 9/0024* (2013.01); *A61M 31/00* (2013.01);
(Continued)

(58) Field of Classification Search
CPC ........ A61M 2025/0018; A61M 31/002; A61M 31/00; A61M 31/007; A61M 37/0069;
(Continued)

(56) References Cited

U.S. PATENT DOCUMENTS 4,402,693 A * 9/1983 Roseman ............ A61M 31/002
424/430
5,074,857 A * 12/1991 Shepherd ............. A61K 9/0068
424/438

(Continued)

FOREIGN PATENT DOCUMENTS

GB   2155889 A   10/1955
WO   9842317 A2   10/1998
(Continued)

OTHER PUBLICATIONS

International Search Report and the Written Opinion of the International Searching Authority for PCT/US2014/020703 dated Jun. 13, 2014.

*Primary Examiner* — Bradley J Osinski
*Assistant Examiner* — Nilay Shah
(74) *Attorney, Agent, or Firm* — Eversheds Sutherland (US) LLP

(57) ABSTRACT

A drug delivery device is provided. In an embodiment, the device includes a device body having an elongated drug reservoir lumen, a drug positioned in the drug reservoir lumen, and at least one end plug positioned at an end of the device body, for example inserted in an end of the drug reservoir lumen. The end plug may include an aperture therethough, and the drug delivery device may be configured
(Continued)

to release the drug from the drug reservoir lumen through the aperture.

22 Claims, 17 Drawing Sheets

(52) U.S. Cl.
CPC ....... *A61M 31/007* (2013.01); *A61M 37/0069* (2013.01); *A61M 2205/0216* (2013.01); *A61M 2205/04* (2013.01); *A61M 2210/1085* (2013.01); *A61M 2210/1089* (2013.01)

(58) Field of Classification Search
CPC .. A61M 2210/1089; A61M 2210/1085; A61M 27/008; A61M 25/0041; A61K 9/0024; A61K 9/0034; A61K 9/0036; A61K 9/0039; A61K 9/0065
See application file for complete search history.

(56) References Cited

U.S. PATENT DOCUMENTS

| | | | |
|---|---|---|---|
| 5,629,008 A | 5/1997 | Lee | |
| 6,171,298 B1 | 1/2001 | Matsuura et al. | |
| 6,923,800 B2 * | 8/2005 | Chen | A61K 9/0004 604/892.1 |
| 8,343,516 B2 | 1/2013 | Daniel et al. | |
| 8,679,094 B2 | 3/2014 | Cima et al. | |
| 8,801,694 B2 | 8/2014 | Lee et al. | |
| 9,017,312 B2 | 4/2015 | Lee et al. | |
| 9,107,816 B2 | 8/2015 | Lee et al. | |
| 2004/0111080 A1 | 6/2004 | Harper et al. | |
| 2004/0260272 A1 | 12/2004 | Friedman et al. | |
| 2005/0070884 A1 | 3/2005 | Dionne et al. | |
| 2009/0149833 A1 * | 6/2009 | Cima | A61K 9/0024 604/517 |
| 2009/0202608 A1 | 8/2009 | Alessi et al. | |
| 2010/0330149 A1 * | 12/2010 | Daniel | A61K 9/0034 424/430 |
| 2010/0331770 A1 | 12/2010 | Lee et al. | |
| 2011/0060309 A1 * | 3/2011 | Lee | A61K 9/0034 604/500 |
| 2011/0106006 A1 * | 5/2011 | Martin | A61K 9/0024 604/93.01 |
| 2012/0089122 A1 | 4/2012 | Lee et al. | |
| 2012/0203203 A1 | 8/2012 | Lee et al. | |
| 2013/0324946 A1 | 12/2013 | Tobias et al. | |
| 2014/0276636 A1 | 9/2014 | Lee et al. | |

FOREIGN PATENT DOCUMENTS

| | | |
|---|---|---|
| WO | 2013177068 A1 | 11/2013 |
| WO | 2014144066 A1 | 9/2014 |
| WO | 2015026813 A1 | 2/2015 |
| WO | 2015069723 A1 | 5/2015 |

* cited by examiner

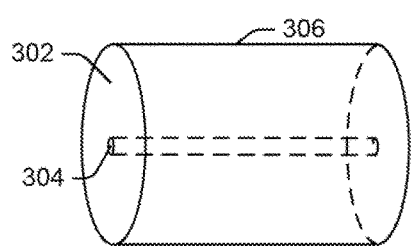
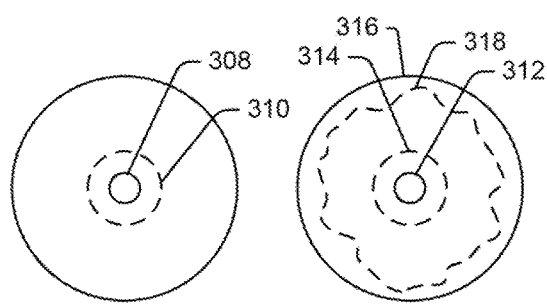
FIG. 17A  FIG. 17B  FIG. 17C
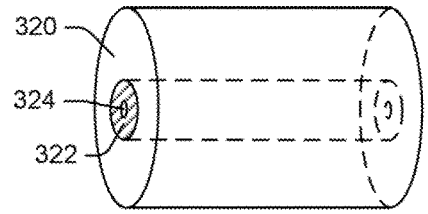
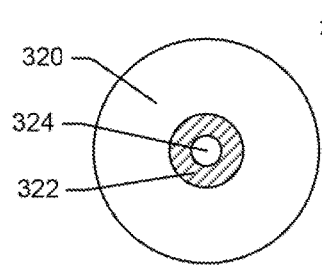
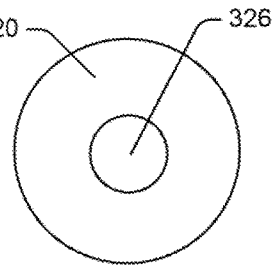
FIG. 17D  FIG. 17E  FIG. 17F
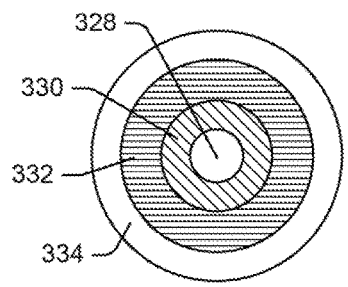
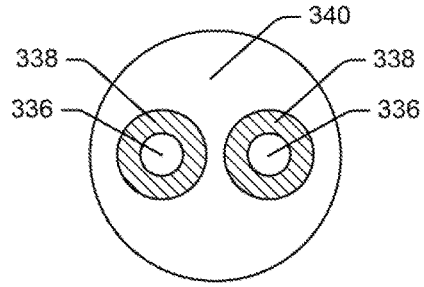
FIG. 17G  FIG. 17H
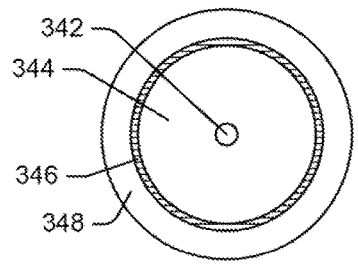
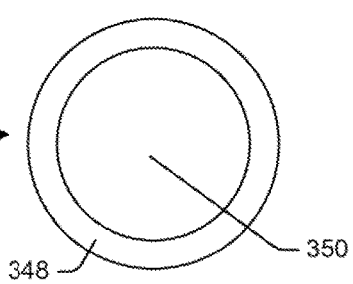
FIG. 17I  FIG. 17J

DRUG DELIVERY DEVICES AND METHODS FOR CONTROLLED DRUG RELEASE THROUGH DEVICE ORIFICE

CROSS-REFERENCE TO RELATED APPLICATION

This application claims priority to and benefit of U.S. Provisional Application No. 61/772,751, filed Mar. 5, 2013, which is incorporated herein by reference in its entirety.

BACKGROUND

This disclosure is generally in the field of implantable medical devices and methods, including but not limited to drug delivery devices deployable within the urinary bladder.

Targeted delivery of drug to the local or regional tissue sites where the drug is needed continues to have room for improvement in a variety of diseases and conditions in humans and other mammals. This is particularly true for tissue sites that are not readily accessible to the physician, where controlled release of drug is needed over an extended period, where a sufficient amount of drug can be stored on-board an implantable device having a relatively small volume, and/or where device is deployable with minimally invasive systems and methods and provides minimal patient discomfort. The devices should be relatively simple in their construction and operation, to provide a robust device, reliable drug delivery, and cost effective device construction and assembly.

Implantable medical devices are described in patent application publications US 2010/0331770, US 2011/0152839, US 2012/0089122, and US 2012/0203203, which are incorporated herein by reference. Some of the devices described have one or more apertures, or orifices, through which drug is released from the device. It would be desirable to have alternative and/or improved devices and methods that use release orifices in the course of providing controlled release of drug in vivo. For example, it would be desirable to reduce or avoid the manufacturing cost associated with laser drilling microscale orifices in silicone tubing.

In some drug delivery devices that rely on diffusion, osmosis or a combination thereof, it may be difficult for the device to dispense the entire drug from the reservoir. This problem may be magnified where the drug, such as some anti-cancer drugs, are extremely expensive to produce. Accordingly, it would be desirable to make sure that all or most of the drug provided in the device actually is released from the device during a treatment period.

SUMMARY

In one aspect, a drug delivery device is provided which includes a device body that includes an elongated drug reservoir lumen and a retention frame lumen; a drug positioned in the drug reservoir lumen; a retention frame positioned at least partly in the retention frame lumen; and at least one end plug positioned at an end of the device body. The retention frame is or includes an elastic wire, and the end plug includes a cavity configured to receive an end portion of the elastic wire. The end plug optionally may include an aperture extending therethrough.

In another aspect, a drug delivery device is provided for insertion into the bladder of a patient. The device includes a device body that includes an elongated drug reservoir lumen; a drug positioned in the drug reservoir lumen; and at least one polymeric end plug positioned at an end of the device body. The end plug includes an aperture therethough, and the device is configured to release the drug from the drug reservoir lumen through the aperture.

In still another aspect, a drug delivery device is provided that includes a device body comprising an elongated drug reservoir lumen; a drug positioned in the drug reservoir lumen; and at least one end plug positioned at an end of the device body, the end plug comprising an aperture therethough, wherein the aperture is defined by a bioerodible material configured to degrade in vivo such that the opening of the aperture effective for drug release increases as drug is released. For example, the aperture has a cross-sectional open area (perpendicular to the direction of flow through the aperture) that enlarges over the course of drug release. In addition or in the alternative, the length of the aperture (in the direction of flow through the aperture) may decrease over the course of drug release.

BRIEF DESCRIPTION OF THE DRAWINGS

FIGS. 17A-17S show various embodiments of device end plugs with different designs of erodible orifices.

DETAILED DESCRIPTION

The devices, systems, and methods disclosed herein build upon those described in the following patent application publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); and US 2007/0202151 (Lee et al.), which are incorporated by reference herein. The improvements and developments are described below and illustrated in the attached figures.

I. The Insertable Drug Delivery Device

Figure 1:
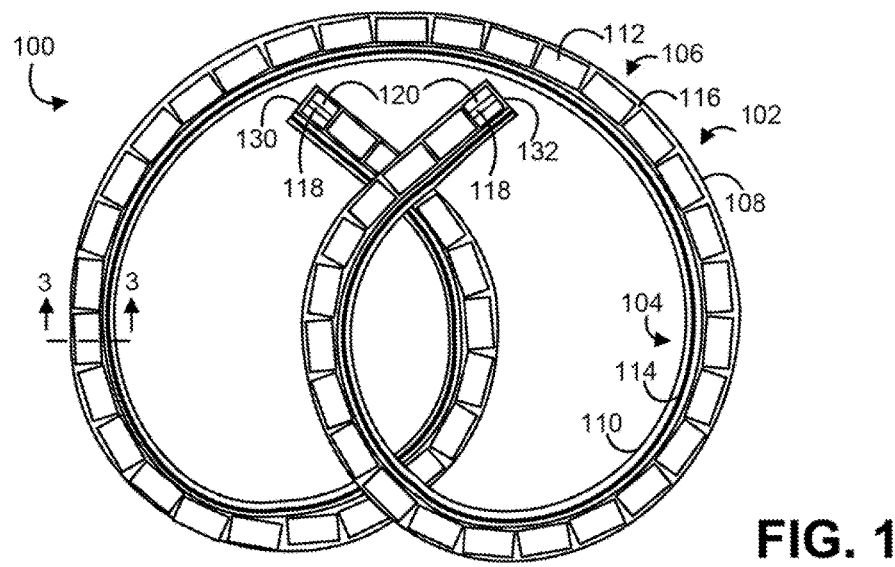
FIG. 1 is a plan view of an embodiment of a drug delivery device according to one embodiment.
Figure 2:
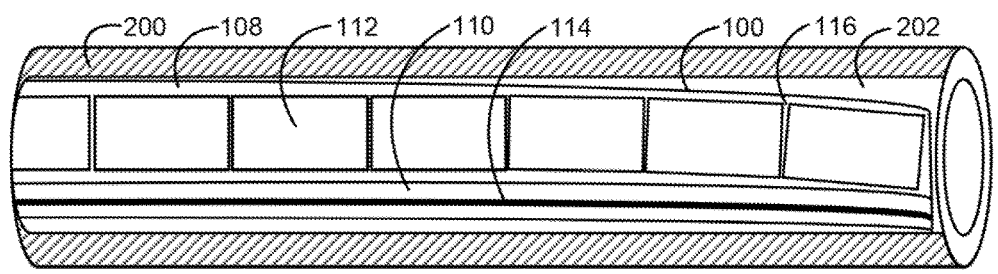
FIG. 2 is a plan view of the drug delivery device shown in FIG. 1, illustrating the drug delivery device inside a deployment instrument.

An embodiment of a drug delivery device 100 is illustrated in FIG. 1. The device 100 includes a drug reservoir portion 102 and a retention frame portion 104. In FIG. 1, the device 100 is shown in a relatively expanded shape suited for retention within the body of a patient (for example in the urinary bladder of the patient). In FIG. 2, the device 100 is shown in a relatively lower-profile shape for deployment through the channel 200 of a deployment instrument, such as a cystoscope or other catheter, e.g., for insertion into and through the urethra and into the bladder of the patient. Following deployment (release of the device) into the body, the device 100 may assume the relatively expanded shape to retain the drug delivery device in the body cavity or lumen.

For the purposes of this disclosure, terms such as "relatively expanded shape," "relatively higher-profile shape," or "retention shape" generally denote any shape suited for retaining the device in the intended insertion location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including the linear or elongated shape shown in FIG. 2 that is suited for deploying the device through the working channel of catheter, cystoscope, or other deployment instrument positioned in a lumen of the body, such as the urethra. In some embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

The drug delivery device 100 includes an elastic or flexible device body 106 that defines a drug reservoir lumen 108 and a retention frame lumen 110. The drug reservoir lumen 108 is designed to house a drug formulation, such as a number of solid drug units 112, to form the drug reservoir portion 102. The retention frame lumen 110 is designed to house a retention frame 114 to form the retention frame portion 104. The illustrated lumens 108, 110 are discrete from each other, although other configurations are possible.

Figure 3:
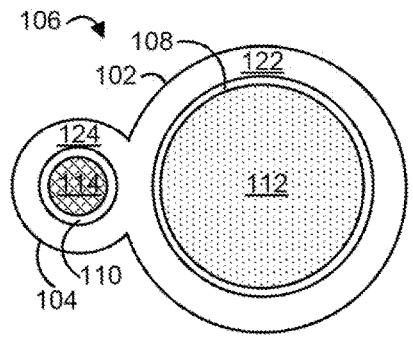
FIG. 3 is a cross-sectional view of the drug delivery device shown in FIG. 1, taken along line 3-3 in FIG. 1.

As shown in the cross-sectional view of FIG. 3, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed. In one example, the wall 122 of the drug reservoir lumen 108 has an inner diameter of about 1.5 mm and an outer diameter of about 1.9 mm, while the wall 124 of the retention frame lumen 110 has an inner diameter of about 0.5 mm and an outer diameter of about 0.9 mm. However, the inner and outer diameters of the wall 122 of the drug reservoir lumen 108 and the wall 124 of the retention frame lumen 110 may be any suitable diameter. The cross-sectional area of the entire body of the device 106 may be about 0.035 $cm^2$ or less. However, the cross-sectional area of the entire body of the device 106 may be any suitable dimension.

As shown in FIG. 1, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. The drug units may, for example, be tablets or capsules. However, essentially any number of drug units may be used, depending upon the sizes of the reservoir and the drug units. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly, such as by a flow of pressurized gas, in which case the exit 132 provides egress for the flow of pressurized gas to escape from the drug reservoir lumen 108.

Once the drug units 112 are loaded, end plugs 120 block the entry 130 and exit 132. The end plugs 120 may be cylindrical plugs inserted into the entry 130 and the exit 132. In some instances, each of the end plugs 120 may have a slightly larger outer diameter than an inner diameter of the drug reservoir lumen 108 so that the plugs substantially enclose the entry 130 and exit 132 and are snugly retained in position. In other instances, the end plugs 120 may have an outer diameter that is the same as or slightly smaller than an inner diameter of the drug reservoir lumen 108. Such a configuration may provide tolerances for the end plugs 120 to swell. For example, the end plugs 120 may swell in vivo when in contact with bodily fluid, such as urine in the bladder. In other instances, the end plugs 120 may be secured within the drug reservoir lumen 108 by an adhesive.

In still other instances, the end plugs 120 may be secured within the drug reservoir lumen 108 by an external clamp disposed about the drug reservoir lumen 108. The end plugs 120 may be secured within the drug reservoir lumen 108 by any means disclosed herein or a combination thereof.

One or both of the end plugs 120 includes an aperture 118 to provide a passageway for releasing drug (from the drug units) from the drug reservoir lumen 108 as discussed in greater detail below. In some instances, the dimensions of the aperture in the end plugs 120, such as the diameter or length, may change during the use of the drug delivery device 100. For example, the diameter of the aperture in the end plugs 120 may increase over time, or the length of the aperture may decrease over time, for example due to dissolution or bioerosion of the material defining the aperture.

In certain embodiments, each of the end plugs 120 may include a cavity for receiving an end portion of the retention frame 114 as discussed in greater detail below. In some cases, a number of end plugs 120 can be positioned in the entry 130 or the exit 132. The end plugs 120 may be silicone plugs. In embodiments where one of the end plugs 120 is omitted, the entry 130 or exit 132 without the end plug 120 may be closed with any other suitable biocompatible material. In one example, the material is an adhesive substance that is placed in the drug reservoir lumen 108 in workable form and cures therein.

The retention frame lumen 110 is loaded with the retention frame 114, which may be an elastic wire. The retention frame 110 may be configured to spontaneously return to a retention shape, such as the illustrated example "pretzel" shape or another coiled shape, such as those disclosed in the patent publications described above. In particular, the retention frame 114 may serve to retain the device 100 in the body of a patient, such as in the bladder. For example, the retention frame 114 may have an elastic limit and modulus that allows the device 100 to be introduced into the body in a relatively lower-profile shape, permits the device 100 to return the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once inserted, limiting or prevent accidental expulsion.

The material used to form the device body 106 may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The material used to form the device body 106 also may be water permeable or porous so that solubilizing fluid (e.g., urine or other bodily fluid) can enter the drug reservoir portion 102 to solubilize the drug units 112 once the device is inserted. For example, silicone or another biocompatible elastomeric material may be used.

In one embodiment, in which the drug delivery device 100 is designed to be inserted in the bladder, the drug delivery device 100 is designed to be inserted into (and optionally retrieved from) the bladder through the urethra cystoscopically. Thus, the device may be sized and shaped to fit through a narrow tubular path of a deployment instrument, such as a catheter or cystoscope.

The exact configuration and shape of the intravesical drug delivery device may be selected depending upon a variety of factors including the specific site of deployment/insertion, route of insertion, drug, dosage regimen, and therapeutic application of the device. The design of the device may minimize the patient's pain and discomfort, while locally delivering a therapeutically effective dose of the drug to a tissue site (e.g., urothelial tissue) in a patient.

The Drug Reservoir Portion

In one embodiment, the drug reservoir portion of the device includes an elongated tube. An interior of the tube may define one or more drug reservoirs, and a drug formulation may be housed in the drug reservoir(s). In another embodiment, the drug reservoir portion is in a form other than a tube.

The release rate of the drug from the drug reservoir portion generally is controlled by the design of the combination of the device components, including but not limited to the materials, dimensions, surface area, and one or more apertures of the drug reservoir portion and/or the end plugs, as well as the particular drug formulation and total mass of drug load, among others.

An example of such a drug reservoir portion is shown in FIGS. 1-3. As shown, the drug reservoir portion 102 may include a body formed from an elastomeric tube 122. The tube 122 defines a reservoir 108 that contains a number of drug units 112. Ends of the tube 122 are closed off with end plugs 120.

In one embodiment, the drug reservoir portion operates as an osmotic pump. In such embodiments, the tube may be formed from a water permeable material, such as a silicone, or tube may have a porous structure, or both. Following insertion of the device into the patient, water or urine permeates through the wall of the tube, one or more apertures formed through the end plug and/or the tube wall, or one or more passing pores formed through a porous tube. The water enters the reservoir, and is imbibed by the drug formulation. In some instances, solubilized drug is dispensed at a controlled rate out of the reservoir through the one or more apertures associated with the end plugs, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures in the end plugs; and the drug formulation dissolution profile, among other factors. In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Publication No. 2009/0149833.

In an alternative embodiment, the device may operate essentially by diffusion of the drug from the tube through the one or more discrete apertures or passing pores formed in the end plugs. In one embodiment, the drug diffuses only through one or more apertures in the end plug(s). In another embodiment, the drug diffuses both through one or more apertures in the end plug(s) and also through the sidewall of the tube defining the drug reservoir, or through an aperture defined in the sidewall.

In still other embodiments, the device may operate by a combination of osmosis and diffusion. For example, where release of a first portion of the drug is predominantly or exclusively driven by osmotic pressure, and release of a second portion of the drug is predominantly or exclusively driven by diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical insertion, as described in further detail below.

In a preferred embodiment, the drug reservoir portion is formed from a material that is both elastomeric and water permeable. One material that is both elastomeric and water permeable is silicone, although other biocompatible materials may be used.

The length, diameter, and thickness of the tube may be selected based on the volume of drug formulation to be contained, the desired rate of delivery of the drug from the tube, the intended site of insertion of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of medical grade silicone tubing, as known in the art. Other suitable non-resorbable materials may be used. In some embodiments, the device body is bioerodible. In one embodiment of a bioerodible device, the tube of the body is formed of a biodegradable or bioresorbable polymer. Any suitable polymers may be used.

The tube of a drug reservoir portion tube may be substantially linear and in some cases may be substantially cylindrical with a circular cross-section, although polygonal cross-sectional shapes can be used, among others.

In one embodiment, the tube has multiple reservoirs. Each reservoir may be defined by a portion of the tube inner surface and at least one partition structure inserted into the tube. The partition structure may have a larger cross-section than the tube, securing the partition structure in place and segregating adjacent reservoirs. The partition may be non-porous or semi-porous, non-resorbable or resorbable and may be formed of a material described herein with reference to the end plug 120. The partition also may be formed in the tube, such as by molding. For example, one or more webs may extend through the tube along its length to segregate axial reservoirs that extend along the length of the tube. The partition also may be a structure that joins two different tubes that serve as separate reservoirs.

The multiple reservoirs permit segregating two or more different drug formulations in different reservoirs, delivering a single drug from different reservoirs at different rates or times following insertion, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

For example, the onset of release of two doses in different reservoirs can be staged by configuring the device accordingly, such as by using different materials for portions of the tube defining different reservoirs, by associating the aperture(s) of different reservoirs with different timing membranes, by placing drugs with different solubilities in the reservoirs, or by placing drugs with different forms in the reservoirs, such as a liquid form for immediate release and a solid form to be solubilized prior to release. Thus, the device may release some drug relatively quickly after insertion while other drug may experience an induction time before beginning release.

In one embodiment, the total volume of the reservoir (or combined reservoirs) is sufficient to contain all of the drug needed for local delivery over the course of a single treatment, reducing the number of procedures needed to treat a particular condition.

The term "drug" as used herein encompasses any suitable pharmaceutically active ingredient. The drug may be small molecule, macromolecule, biologic, or metabolite, among other forms/types of active ingredients. The drug described herein includes its alternative forms, such as salt forms, free acid forms, free base forms, and hydrates. The drug may be formulated with one or more pharmaceutically acceptable excipients known in the art. Non-limiting examples of the drug include gemcitabine, oxaliplatin, and/or another chemotherapeutic agent; trospium and/or another antimuscarinic agent; and/or lidocaine and/or another anesthetic agent. In one embodiment, the first compartment may be loaded with two or more types of drug tablets (e.g., different drugs), so that a combination of drugs may be delivered.

In embodiments, the drug is one used to treat pain. A variety of anesthetic agents, analgesic agents, and combinations thereof may be used. In one embodiment, the drug is an anesthetic agent. The anesthetic agent may be a cocaine analogue. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocalne, ropivacaine, and trimecaine. Representative examples of aminoesters or ester-class anesthetics include amylocalne, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. The drug also can be an antimuscarinic compound that exhibits an anesthetic effect, such as oxybutynin or propiverine. In embodiments, the analgesic agent includes an opioid. Representative examples of opioid agonists include alfentanil, allylprodine, alphaprodine, anileridine, benzyl morphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, di methylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated. Representative examples of other suitable pain relieving agents include such agents as salicyl alcohol, phenazopyridine hydrochloride, acetaminophen, acetylsalicylic acid, flufenisal, ibuprofen, indoprofen; indomethacin, naproxen.

In certain embodiments, the drug is one used to treat inflammatory conditions such as interstitial cystitis, radiation cystitis, painful bladder syndrome, prostatitis, urethritis, post-surgical pain, and kidney stones. Non-limiting examples of drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

In certain embodiments, the drug is one used to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutylin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In certain embodiments, the drug is one used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In certain embodiments, the drug is one used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In certain embodiments, the drug is one used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

In certain embodiments, the drug is one used to treat neurogenic bladder. Representative examples of such drugs include analgesics or anaesthetics, such as lidocaine, bupivacaine, mepivacaine, prilocalne, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; α-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., Spinal Cord 42:267-72 (2004).

In certain embodiments, the drug is one used to treat incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include α-adrenergic agonists, estrogens, β-adrenergic agonists, tricyclic antidepressants (imipramine, amitriptyline). In still another embodiment, the drug is selected from those known for facilitating bladder emptying (e.g., α-adrenergic antagonists (phentolamitie) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., M3 muscarinic agonist, choline ester).

End Plugs

Figure 4A:
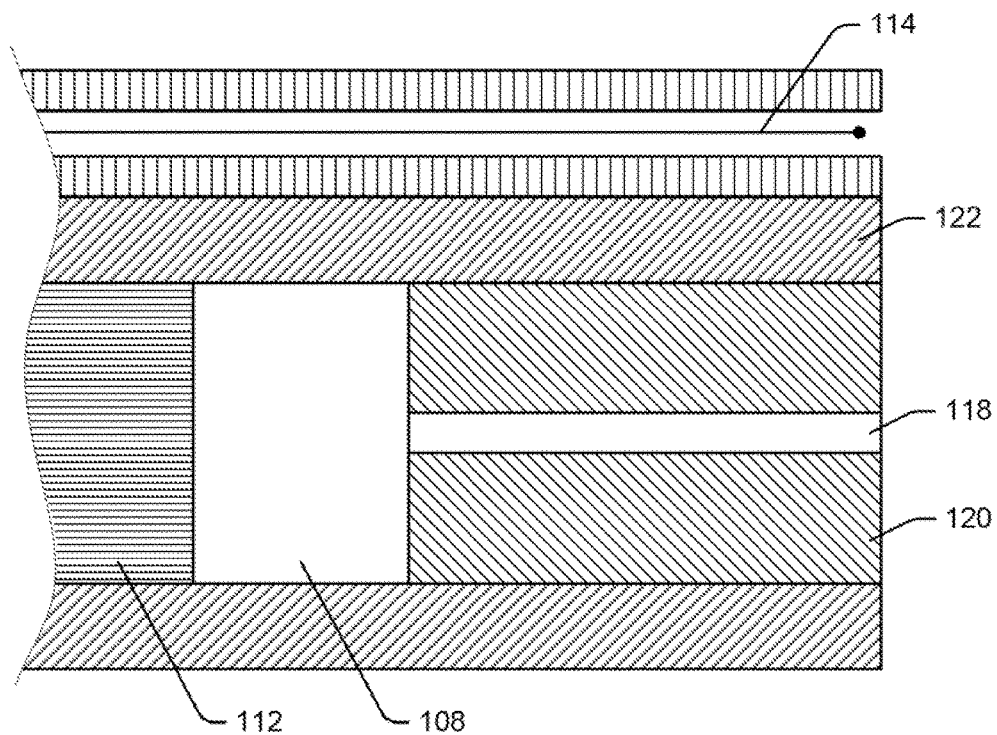
FIG. 4A is a cross-sectional view of an end portion of the drug delivery device according to one embodiment.

The end plugs, or plug components, may have any shape suited to wholly or partially plug or close the tube end, such as a cylinder 120 as shown in FIG. 1 and FIG. 4A, a ball, a disk, or others. In some embodiments, the end plug may have a sealing structure portion that has a larger diameter than the inner diameter of the tube, such that the tube stretches to fit snugly about the sealing structure, closing the tube and retaining the sealing structure in place. In other instances, the end plugs 120 may be secured within the drug reservoir lumen 108 by an adhesive and/or by an external clamp. In yet other embodiments, the end plugs 120 may be secured within the drug reservoir lumen 108 by one or more wall structures described in U.S. provisional application No. 61/799,733.

In a preferred embodiment, the drug units 112 are disposed flush with the end plugs 120. That is, at least one of the drug units is immediately adjacent to the interior end of the end plug. This may advantageously minimize the lag time before drug release begins following insertion into the patient. In an alternative embodiment, the drug units 112 are spaced apart from the end plugs 120. Similarly, the drug units 112 may be disposed flush with other drug units 112 or spaced apart from other drug units 112. The less space between the drug units 112 and/or the end plugs 120 reduces lag time before drug release begins.

The end plug may be formed from biocompatible material, including a metal such as stainless steel, a polymer such as silicone, a ceramic, sapphire, or adhesive, among others or combinations thereof. The material may be biodegradable or bioerodible. In a preferred embodiment, the plug is formed of a relatively stiff thermoplastic polymer, such as polyethylene.

Figure 4B:
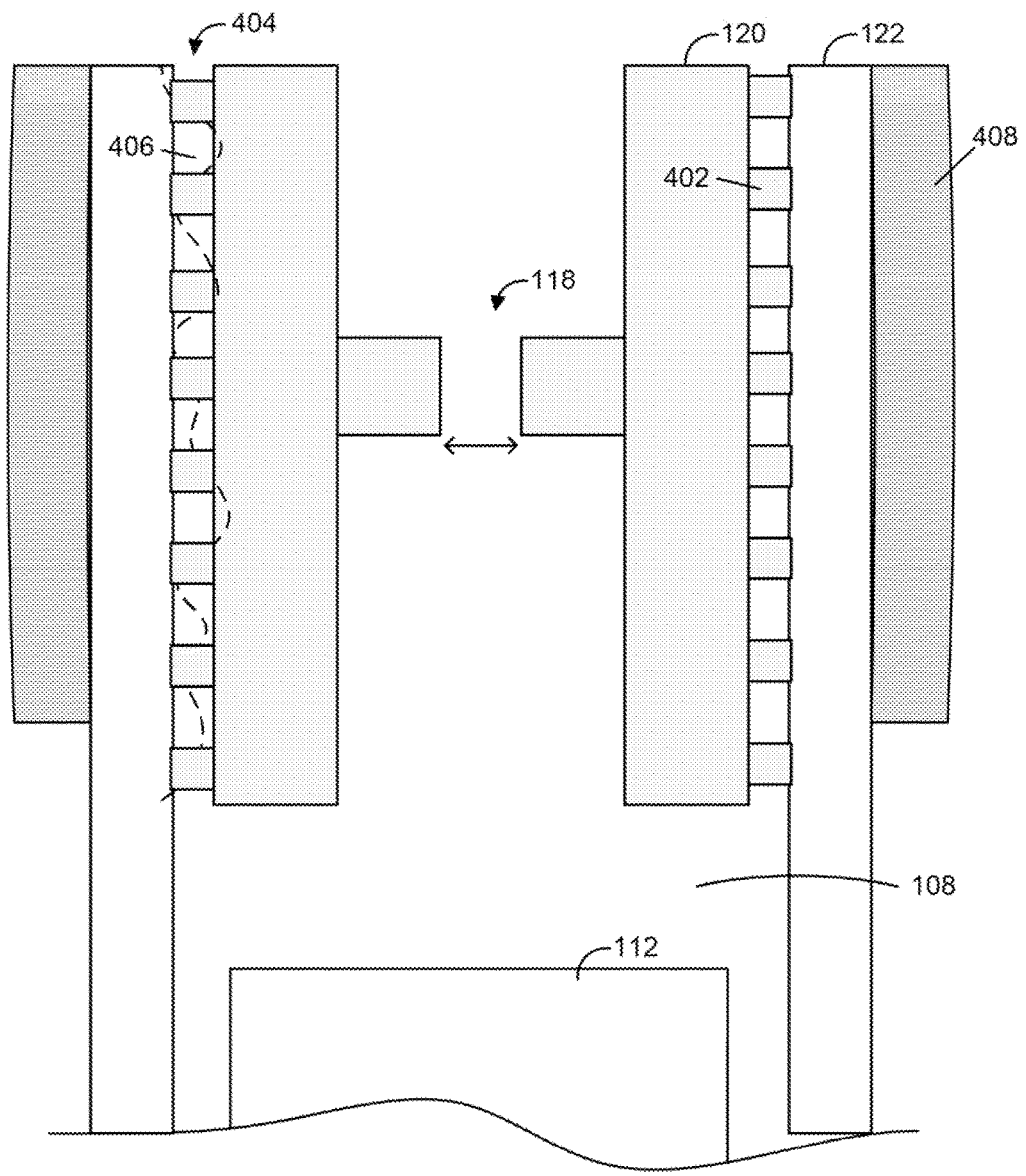
FIG. 4B is a cross-sectional view of an end portion of the drug delivery device according to another embodiment.

As depicted in FIG. 4B, the end plugs 120 may include one or more oversized ribs 402 about the diameter of the end plugs 120 to further facilitate a snug fit within the tube 122. In other instances, the end plugs 120 may be secured within the drug reservoir lumen 108 by an adhesive 404. For example, the end plugs 120 may include one or more channels or grooves 406 disposed circumferentially about the end plugs 120, with the channels 406 being configured to receive an adhesive bead therein. That is, the adhesive 404 may be applied to the channel 406, and the end plugs may be inserted into the drug reservoir lumen 108. In this manner, the channel 406 may provide a region for the adhesive 402 to bond with the end plugs 120 and an interior of the tube 122 such that the end plugs 120 may be secured within the drug reservoir lumen 108. The channel 406 may be disposed about the end plugs 120 in any orientation, such as, for example, circumferentially, axially, or a combination thereof. Moreover, the channel 406 may be a slot formed within the end plugs 120, or the channel 406 may be formed by two or more ribs 402 associated with the end plugs 120. In some instances, the channel 406 may be omitted completely. Any combination of the described securing means may be used.

In another embodiment, the end plugs 120 may be secured within the drug reservoir lumen 108 mechanically. That is, in one embodiment, the end plugs 120 may be secured within the drug reservoir lumen 108 by an external clamp 408 disposed about the tube 122. For example, the end plugs 120 may be positioned within the end portions of the drug reservoir lumen 108, such as entry 130 and/or exit 132, and a clamping means, such as clamp 408, may be disposed about the tube 122. In one embodiment, the clamp is a heat-shrunk polymeric tube or sheath. In this manner, the clamp 408 may be configured to apply a clamping force about a portion of the drug reservoir lumen 108 such that the end plugs 120 within the entry 130 and/or exit 132 of the drug reservoir lumen 108 are secured in place. Although various example embodiments have been described for securing the end plugs 120 in place, the end plugs 120 may be secured via any means, such as press fitting, adhesive, mechanically, a combination thereof, or the like.

In certain embodiments, each of the end plugs 120 may include an aperture 118 therethrough to provide a passageway for releasing solubilized drug from the drug reservoir lumen 108. The aperture 118 may extend through a center portion of the end plugs 120, or the aperture 118 may extend through any portion of the end plugs 120. That is, the aperture 118 may be off-center. Moreover, the aperture 118 may extend through the end plugs 120 parallel to a center line of the end plugs 120 or at an angle offset therefrom. In some instances, a number of apertures 118 may be used. That is, two or more apertures 118 may extend through the end plugs 120. In other instances, only one of the end plugs 120 may include an aperture 118. The aperture 118 may be formed using any manufacturing techniques, including drilling, laser ablation, punch, molding, or the like. In some instances, the aperture 118 may include a constant diameter along its length. In other instances, the aperture 118 may include varying diameter along its length, such as an hour glass shape or the like. The aperture 118 may be circular, although other shapes are possible and envisioned, with the shape typically depending on manufacturing considerations. The aperture 118 may slightly taper from an exterior to an interior of the tube, and the aperture 118 may be created either before or after the drug is loaded into the tube 122. In some instances, the aperture 118 may include a diameter ranging from about 200 μm to about 1200 μm, although other diameters are possible and envisioned. In other instances, the aperture 118 may include a length ranging from about 5 mm to about 15 mm, although other lengths are possible and envisioned.

In some embodiments, the aperture 118 associated with the end plugs 120 is the only passageway for releasing drug from the drug reservoir lumen 108. However, in another embodiment, the device may include both an aperture 118 associated with one or each of the end plugs 120 and an aperture through a sidewall of the elastomeric tube defining the drug reservoir lumen 108.

Figure 5A:
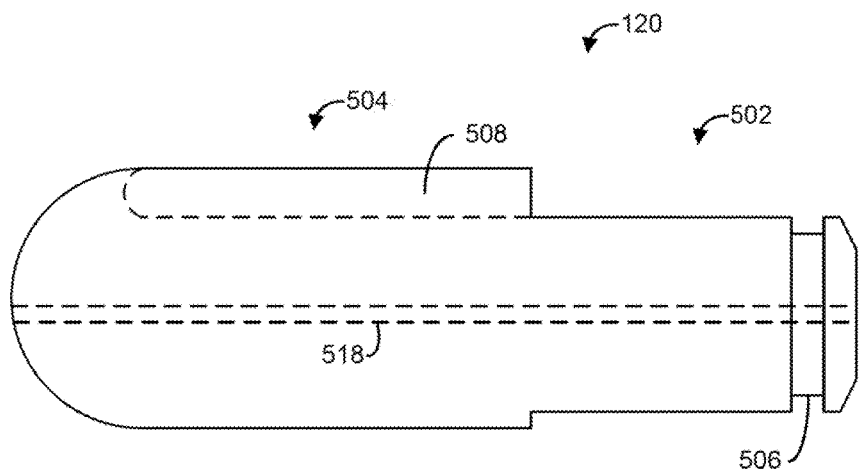
FIG. 5A is a plan view of an end plug of the drug delivery device according to one embodiment.
Figure 5B:
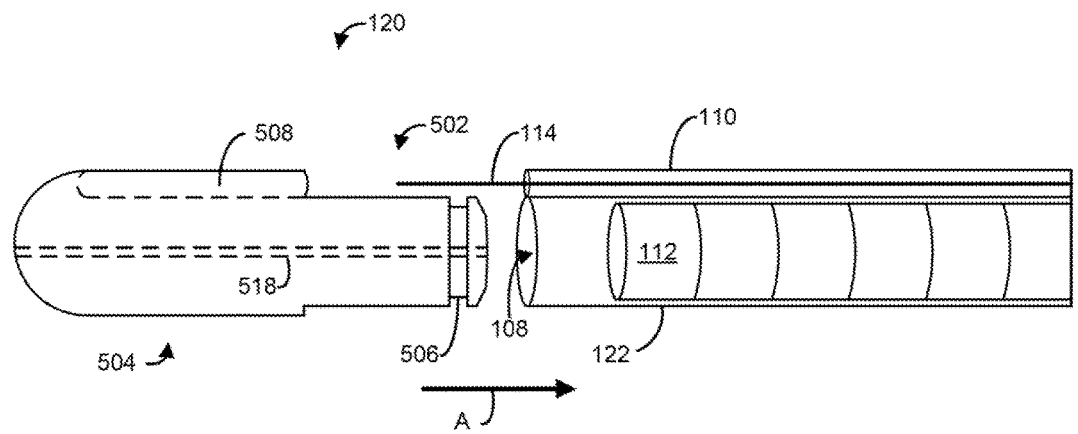
FIG. 5B is a plan view of an end portion of the drug delivery device according to one embodiment.

In a particular embodiment, as depicted in FIGS. 5A and 5B, the end plugs 120 include a proximal portion 502 configured to be positioned within the end portions of the drug reservoir lumen 108, such as entry 130 and/or exit 132, as discussed above in order to seal the ends of the tube 122 to limit escape of the drug units 112. The proximal portion of the end plugs 120 may be secured within the end portions of the drug reservoir lumen 108 via any means described herein, including press fitting, adhesive, mechanically, a combination thereof, or the like. In addition, the end plugs 120 include a distal portion 504 that extends beyond the end portions of the drug reservoir lumen 108. In this manner, a portion of the end plugs 120 may be configured to be position within the tube 122, such as the proximal portion 502, and another portion of the end plugs 120 may be configured to be positioned outside of the tube 122, such as the distal portion 504. In some instances, the proximal portion 502 of the end plugs 120 includes a channel 506, similar to those described above, for receiving an adhesive bead therein. Moreover, in other instances, the proximal portion 502 of the end plugs includes one or more oversized ribs to further facilitate a snug fit within the tube 122. Still further, the proximal portion 502 of the end plugs 120 may be secured by a clamping means as described elsewhere herein. Accordingly, the proximal portion 502 of the end plugs 120 may be secured within the tube 122 by any means described herein or a combination thereof.

In some embodiments, the distal portion 504 of the end plugs 120 also includes a cavity, such as lumen 508, for receiving an end portion of the retention frame 114. In this manner, the lumen 508 encompass the end portion of the retention frame 114 to secure the end portion of the retention frame 114 within the lumen 508 and thereby shielding the pointed tip end of the retention frame 114 and thereby preventing or limiting its ability to damage tissue in vivo or damage the drug reservoir lumen. For example, when the proximal portion 502 of the end plug 120 is inserted into the end portion of the tube 122, as indicated by arrow A, the lumen 508 may abut with the end portion of the retention frame lumen 110 to form a continuous lumen for housing the retention frame 114 therein.

With this embodiment, a metal retention frame wire, such as a nitinol wire, advantageously can be provided without a plasma ball on the end (which is used to provide a blunt end for further lowering the risk of having the wire end puncture tissue or the device) and consequently enables one to temporarily insert a thin, straight tube into the retention frame lumen (and over the retention frame wire) to keep the drug reservoir lumen straight during the process of filling the drug reservoir lumen with drug units.

In some instances, the ends of the distal portion 504 may be rounded or bullet nosed. That is, the ends of the distal portion 504 may be smooth or devoid of edges that may damage tissue. Such configurations may also advantageously facilitate ease of insertion of the device through a deployment instrument and into the bladder or other body lumen of the patient. In FIGS. 5A and 5B, the end plug 120 includes an aperture 518 therethrough to provide a passageway for releasing drug from the drug reservoir lumen 108. That is, the aperture 518 may extend through the end plugs 120 from the proximal portion 502 to the distal portion 504.

Figure 6A:
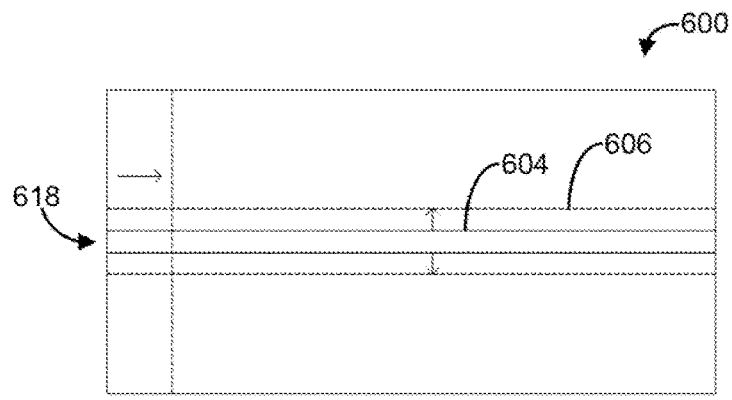
FIG. 6A is a cross-sectional view of an end plug of the drug delivery device according to one embodiment.
Figure 6B:
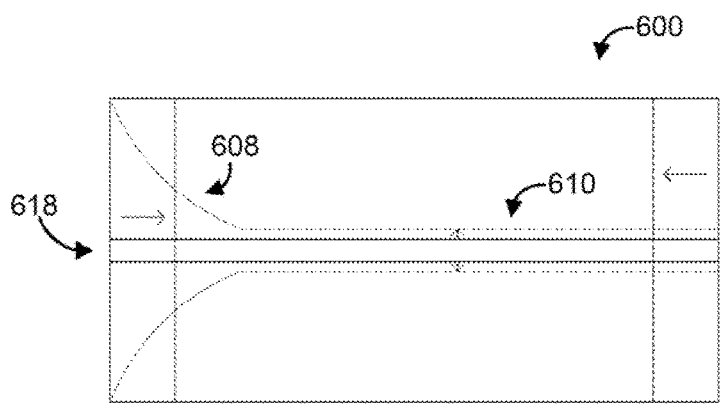
FIG. 6B is a cross-sectional view of an end plug of the drug delivery device according to one embodiment.
Figure 6C:
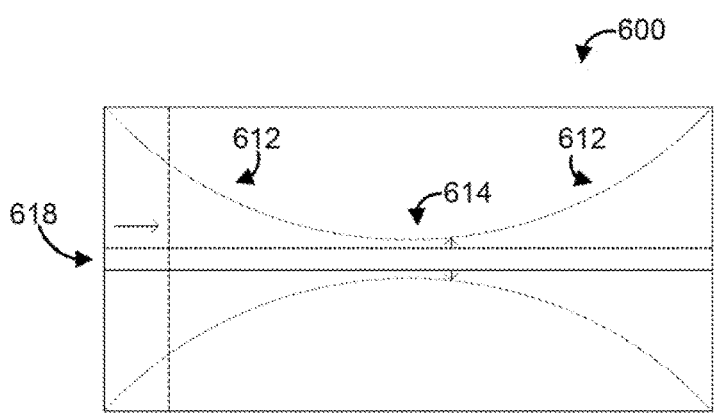
FIG. 6C is a cross-sectional view of an end plug of the drug delivery device according to one embodiment.

As depicted in FIGS. 6A-6C, in certain embodiments, the aperture 618 in the end plugs 600 may be configured to change in vivo over time during the period of use of the drug delivery device. Such a change advantageously may serve as a way to pre-program a change in the release kinetics of the drug or to maintain a desired release profile despite a diminishing concentration of drug within the drug reservoir after much of the drug has already been released. This beneficially may facilitate release of more of the drug from the reservoir over the treatment period, so as to reduce the amount of unreleased, wasted drug.

For example, the aperture 618 in the end plugs 600 may increase over time as indicated by the dashed lines and corresponding arrows. In some instances, as depicted in FIG. 6A, the aperture 618 may include a first diameter 604 that may increase at a constant rate along the length of the aperture 618 to a second diameter 606. In other instances, the diameter of the aperture 618 may increase at a variable rate along the length of the aperture 618. In one example, as depicted in FIG. 6B, the diameter 608 at one end of the aperture 618 may increase at a faster rate than the diameter 610 at other portions of the aperture 618 to form, for example, a trumpet-like structure. The wider diameter 608 portion may face towards or away from the drug units 112. In another example, as depicted in FIG. 6C, the diameter 612 at both ends of the aperture 618 may increase at a faster rate than the diameter 614 at a center portion of the aperture 618. This may result in an aperture 618 that has an hourglass-like configuration. The diameter of the aperture 618 may increase at any rate along the length of the aperture 618 as desired. In addition, in some embodiments, the length of the aperture 618 may decrease over time. For example, as depicted in FIGS. 6A-6C, one or both ends of the aperture 618 may decrease overtime to shorten the length of the aperture 618.

The dynamic aspects of the aperture 618 may facilitate the controlled release of drug from the drug reservoir lumen 108. For example, the end plugs 600 may be erodible, and the release of the drug formulation may be controlled at least in part by the degradation or erosion of the end plugs 600. In some instances, the end plugs 600 partially or wholly degrades over the life of the device. In one instance, the end plugs erode uniformly, such as a straight channel. In another instance, the end plugs erode in an irregular shape, such as open cell foam. The change in the aperture 618 may be gradual or abrupt. In one embodiment, the end plugs 600 includes a degradable polymer, such as poly (D, L-lactic-co-glycolic acid (PLGA) or poly(d,L-lactic acid). The change in the aperture 618 dimensions may be affected by both inner and/or outer pH levels, such as the pH levels within and/or outside of the drug reservoir lumen 108.

Figure 17S:
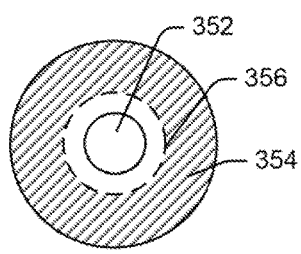
Figure 17S:
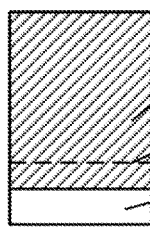
Figure 17S:
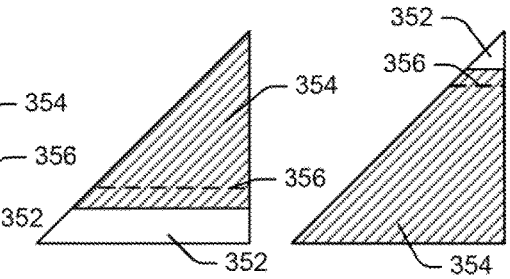
Figure 17S:
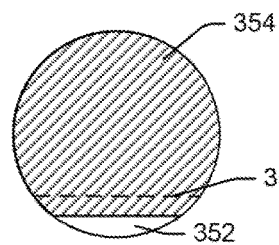
Figure 17S:
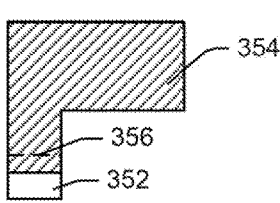
Figure 17S:
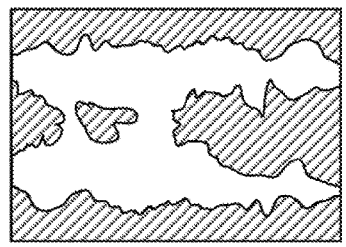
Figure 17S:
Figure 17S:
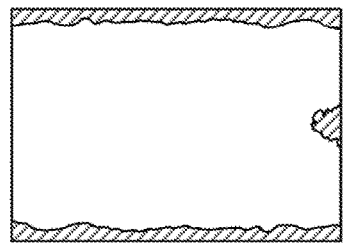
Figure 17S:
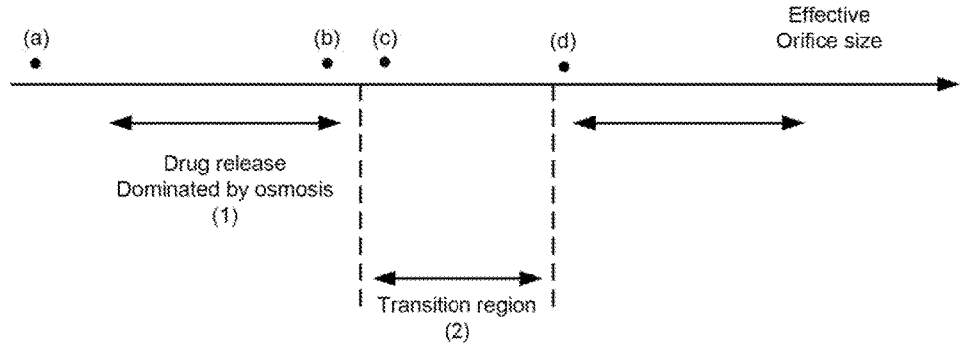

Various changing-orifice embodiments of end plugs (also herein called orifice components or degradable components) are illustrated in FIGS. 17A-17S. For example, FIG. 17A shows an orifice component made of a degradable component 302 having initial opening 304 through the middle of the structure. The outer surface 306 may be joined with the inner side of a tubular drug reservoir with an adhesive, or it may be inserted into such a tubular drug reservoir to create an interference fit if the orifice component outer diameter is larger than the inner diameter of the tube. FIG. 17B shows how degradation occurs in the opening, with the opening diameter changing from an initial size 308 to a larger size 310 after degradation. Outward radial degradation can be uniform or non-uniform along the circumference. FIG. 17C shows how degradation occurs in the opening and over the outer surface, with the opening diameter changing from an initial size 312 to a larger size 314 after degradation, and the outer surface changing from an initial diameter 316 to a smaller, non-uniform diameter 318 after degradation.

FIGS. 17D-17F show the changing orifice size in an orifice component having a degradable core 322 with an initial orifice 324 therethrough and a non-degradable outer structure 320. After complete degradation of the core 322, the release passage for the drug is defined by the inner orifice 326 of the non-degradable structure 320.

FIG. 17G shows another embodiment having a degradable core. Here, the core has multiple core layers that can be made of different materials having different rates of degradation. The degradable core, which has an initial opening 328 is formed by a first degradation layer 330 and a second degradation layer 332. The degradable core is disposed in a non-degradable outer structure 334.

FIG. 17H shows an orifice component having two degradable cores 338, each of which has an initial orifice 336, and a non-degradable outer structure 340. In some embodiments, the outer structure 340 also may be degradable, provided that it degrades at a rate that is slower than that of the core 338.

FIGS. 17I and 17J show an orifice component having an annular degradation layer, which can be degraded to create a sudden increase in orifice size. Initially drug release occurs through orifice 342 until the degradation layer 346 is degraded enough for the core portion 344 to degrade and/or fall out of the larger orifice 350 which is defined within non-degradable structure 348.

FIGS. 17K-17P show various shapes of degradable openings. For example, the degradable openings may be circular, rectangular, triangular, linear, or a combination thereof. The rate of the increase in opening area can be programmed by changing the geometry of the degradable opening. The initial opening 352 is shown with degradable materials 354, and the boundary 356 is shown between the opening and the degradable material after a period of time.

FIGS. 17Q and 17 R show that an embodiment of an orifice component that has a less well-defined aperture geometry, such as a tortuous path (in contrast to a straight channel). As the tortuous path is degraded, a more open orifice is created.

FIG. 17S illustrates that as the "effective" orifice size increases (including both well-defined straight channels and irregular shaped tortuous paths) drug release transforms from osmosis-dominated to diffusion-dominated. The initial size of the orifice can be located anywhere in the line depending on the desired drug release characteristics. For example, if the orifice size is initially set at (a) then drug release, in one embodiment, initially will be dominated by osmosis and take more time to change to a diffusion-dominated region, such as (b), (c), and (d). The transition from (a) to (d) may progress step-wise, e.g., through (b) and (c), or it may change abruptly and directly from (a) to (d) for example if using the mechanism described in 17I and 17J above.

In one embodiment, drug release may be facilitated by a combination of osmosis and diffusion. In this manner, in certain embodiments, as the diameter of the aperture becomes larger, diffusion may become the predominant or sole driving mechanism of drug release.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape is shaped for retention in a body cavity, and the retention frame in the relatively lower-profile shape is shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once inserted. Such a configuration may limit or prevent accidental expulsion of the device from the body under expected forces. For example, the device may be retained in the bladder during urination or contraction of the detrusor muscle.

In embodiments, the retention frame includes or consists of an elastic wire. In one embodiment, the elastic wire is formed of a relatively low modulus elastomer, which may be relatively less likely to irritate or cause ulcer within the bladder or other insertion site and may be biodegradable so that the device need not be removed. In another embodiment, the elastic wire is formed of a superelastic alloy, such as nitinol.

In the embodiment shown in FIGS. 1-2, the retention frame 114 is an elastic wire surrounded by the wall 124 of the retention frame lumen 110, which forms a protective sheath about the retention frame 114. The wall 124 may be formed from a polymer material, such as silicone. In other embodiments, the retention frame is an elastic wire (e.g., formed from a superelastic alloy, such as nitinol) that is covered in a polymer coating such as a silicone sheath, and the coated wire is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIG. 1, the device may occupy a space having dimensions suited to impede expulsion from the bladder. When the retention frame is in the relatively lower-profile shape, such as the elongated shapes shown in FIG. 2, the device may occupy an area suited for insertion into the body, such as through the working channel of a deployment instrument. The properties of the elastic wire cause the device to function as a spring, deforming in response to a compressive load but spontaneously returning to its initial shape once the load is removed.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material or a low modulus material may be used. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as in the range of about 3 N/m to about 60 N/m, or more particularly, in the range of about 3.6 N/m to about 3.8 N/m. Such a spring constant may be achieved with one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or subcircles. The ends of the elastic wire may be adapted to avoid tissue irritation and scarring, such as by being soft, blunt, inwardly directed, joined together, or a combination thereof.

The retention frame may have a two-dimensional structure that is confined to a plane, a three-dimensional structure, such as a structure that occupies the interior of a spheroid, or some combination thereof. Examples of alternative configurations are described in the U.S. patent applications incorporated by reference herein.

II. Use and Applications of the Device

In embodiments, the device is inserted in a patient's body cavity or lumen and subsequently releases one or more drugs for the treatment of one or more conditions. The drug is released locally to one or more tissues at the deployment site and/or regionally to other tissues distal from the deployment site. The release may be controlled over an extended period.

Figure 7A:
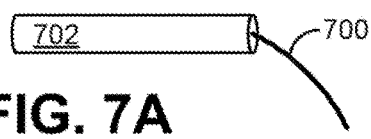
FIGS. 7A-7C illustrates a method of inserting a drug delivery device.
Figure 7B:
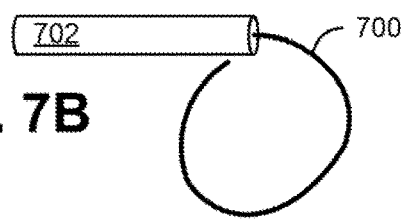
Figure 7C:
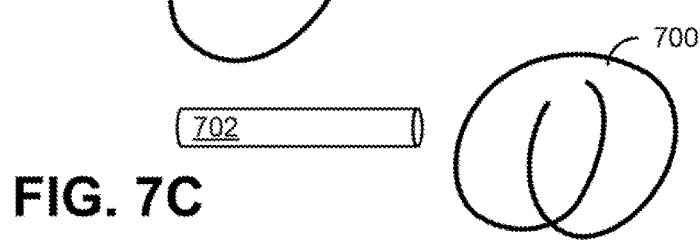

In one example, the device is inserted into the body by passing the drug delivery device through a deployment instrument and releasing the device from the deployment instrument into the body. In one embodiment, the device is inserted into a body cavity such as the bladder, and the device assumes a retention shape, such as an expanded or higher profile shape, once the device emerges from the deployment instrument into the cavity. An example is illustrated in FIGS. 7A-7C, which shows the device 700 assuming a retention shape as the device exits a deployment instrument 702. The deployment instrument 702 may be any suitable lumen device, such as a catheter, urethral catheter, or cystoscope. The deployment instrument 702 may be a commercially available device or a device specially adapted for the present drug delivery devices, for example, as described in U.S. Patent Application Publication No. 2011/0202036.

Once inserted, the device releases the drug. The device may provide extended, continuous, intermittent, or periodic release of a desired quantity of drug over a desired, predetermined period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate and total amount of drug delivered from the device can be selected depending upon the particular drug and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure and/or via diffusion. For example, the drug may be solubilized upon contact with urine in cases in which the device is inserted in the bladder.

Subsequently, the device may be retrieved from the body, such as in cases in which the device is non-resorbable, non-collapsible, or otherwise needs to be removed. In some cases, the device does not need to be retrieved, for example, if the device is resorbed, excreted, or some combination thereof.

The device also may be configured to be completely or partially bioresorbable, such that retrieval is unnecessary. In one case, the device is resorbed or sufficiently degraded that it can be expelled from the bladder during urination. In particular embodiments, the device include biodegradable links such that the device can collapse into a shape that permits passage through the urethra during urination, as described in U.S. Patent Application Publication No. 2012/0089122. In one embodiment, the device is retrieved or resorbed after a portion of the drug, or preferably most or all of the drug, has been released.

Figure 8:
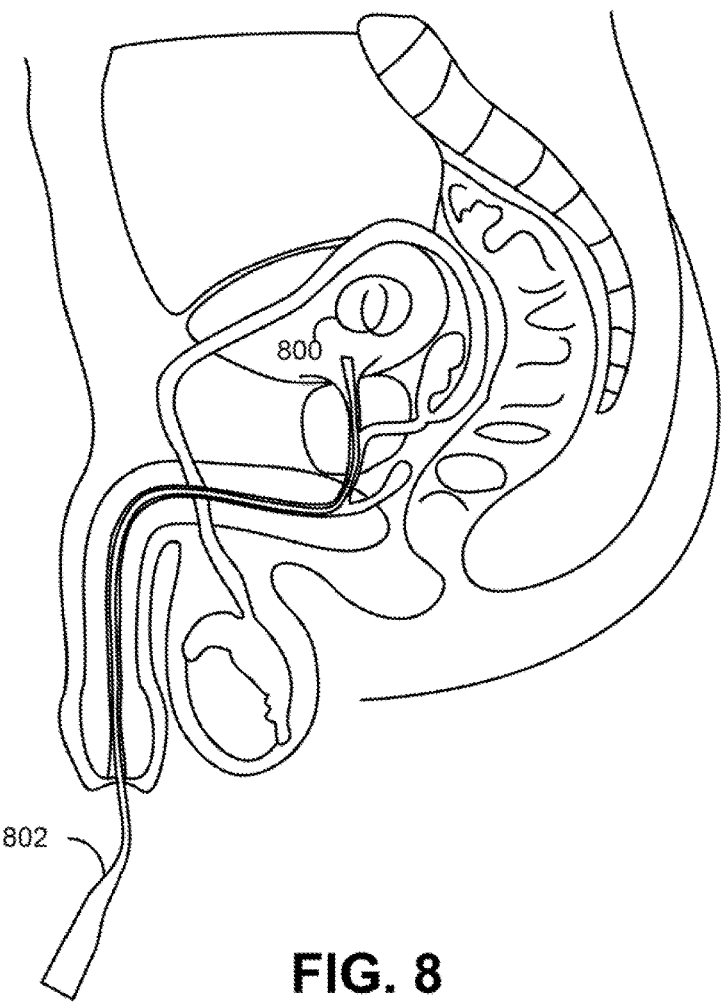
FIG. 8 is a sagittal view of a male patient, illustrating a drug delivery device exiting a deployment instrument into a bladder of the patient according to one embodiment.

FIG. 8 illustrates the insertion of a device 800 into the bladder, wherein the adult male anatomy is shown by way of example. A deployment instrument 802 may be inserted through the urethra to the bladder, and the device 800 may be passed through the deployment instrument 802, driven by a stylet and/or flow of lubricant or other fluid, for example, until the device 800 exits into the bladder. Thus, the device is inserted into the bladder of a male or female human patient in need of treatment.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the medical device, with a self-contained drug payload, is deployed wholly within the bladder to provide sustained delivery of at least one drug to the bladder in an amount that is therapeutically effective for the target tissue in need of treatment. It may be the bladder itself or regionally proximate to the bladder. Such regional delivery may provide an alternative to systemic administration, which may entail undesirable side effects or result in insufficient bioavailability of the drug. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In one embodiment, the intravesical drug delivery device is inserted into a bladder to locally deliver lidocaine or another anesthetic agent for management of pain arising from any source, such as a disease or disorder in genitourinary tissues, or pain stemming from any bladder procedure, such as surgery, catheterization, ablation, medical device implantation/insertion, or stone or foreign object removal, among others.

The present invention may be further understood with reference to the following non-limiting examples.

Example 1: Comparison of In Vitro Release from Devices with Apertures in Tubing Sidewall and Devices with End Plug Apertures Devices were made from silicone tubing housing lidocaine HCl tablets with the dose of 400 mg lidocaine free base equivalent (FBE). In a subset of the devices, the tubing sidewall had a single laser-drilled orifice and the ends were sealed with silicone spacers and adhesive. In the remaining devices, the tubing sidewall had no apertures, and the ends were plugged at one or both ends with custom made silicone orifice end plugs, 5 mm or 15 mm in length. The end plugs, all of which were 2.16 mm OD, were provided with 206 μm, 302 μm, 496 μm, 737 μm, or 1016 μm diameter orifices. Unplugged ends were sealed with a silicone spacer and adhesive. A subset of the devices were loaded with lidocaine HCl tablets with the dose of 450 mg lidocaine free base equivalent (FBE) and sealed at one end with a 5 mm long end plug having a 302 μm diameter orifice.

Figure 9A:
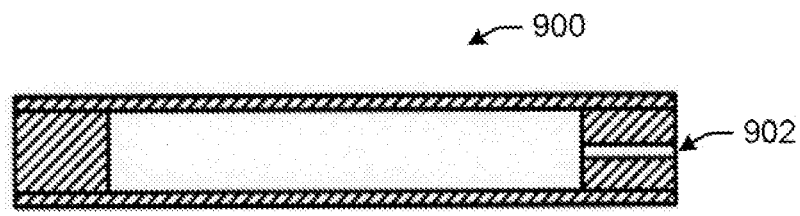
FIG. 9A is a cross-sectional view of one embodiment of a drug delivery device used in an in vitro study.
Figure 9B:
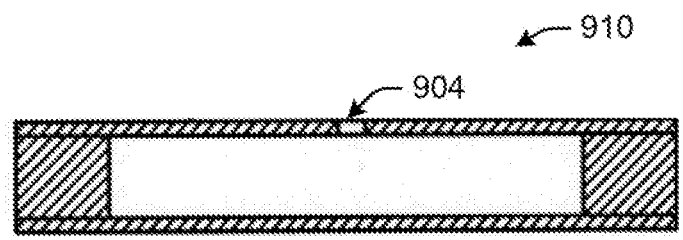
FIG. 9B is a cross-sectional view of another embodiment of a drug delivery device used in an in vitro study.
Figure 9C:
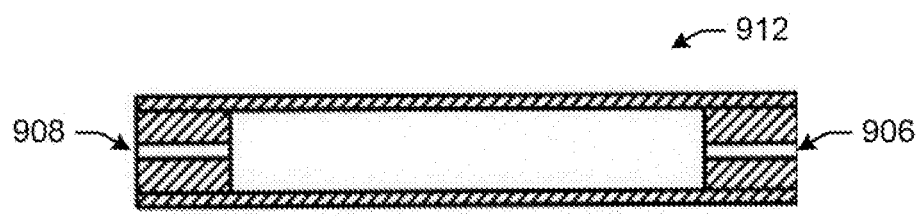
FIG. 9C is a cross-sectional view of still another embodiment of a drug delivery device used in an in vitro study.
Figure 10:
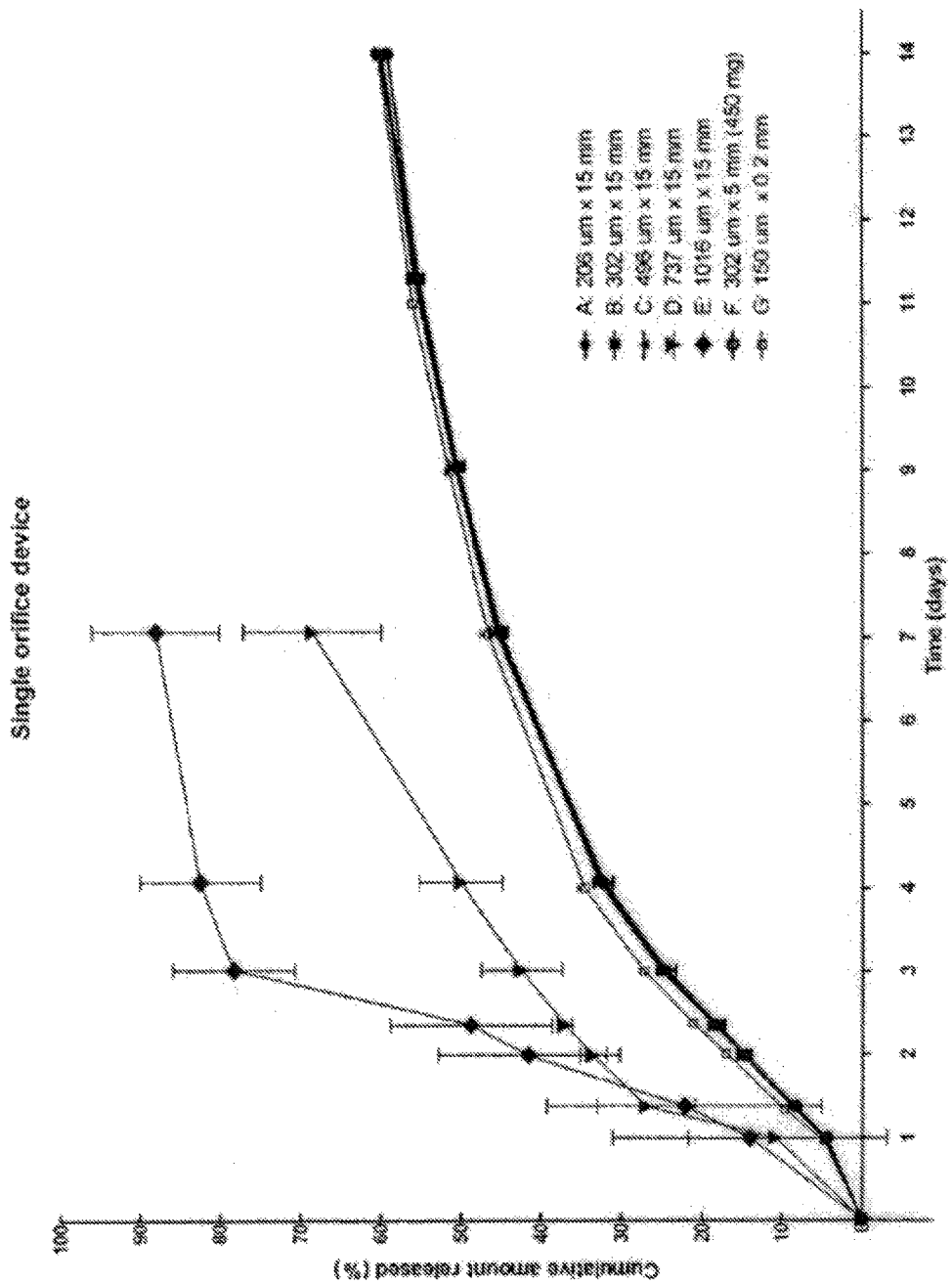
FIG. 10 is a graph of cumulative amount of drug released in vitro from a single orifice system over time for a number of orifice dimensions, according to various embodiments.
Figure 11:
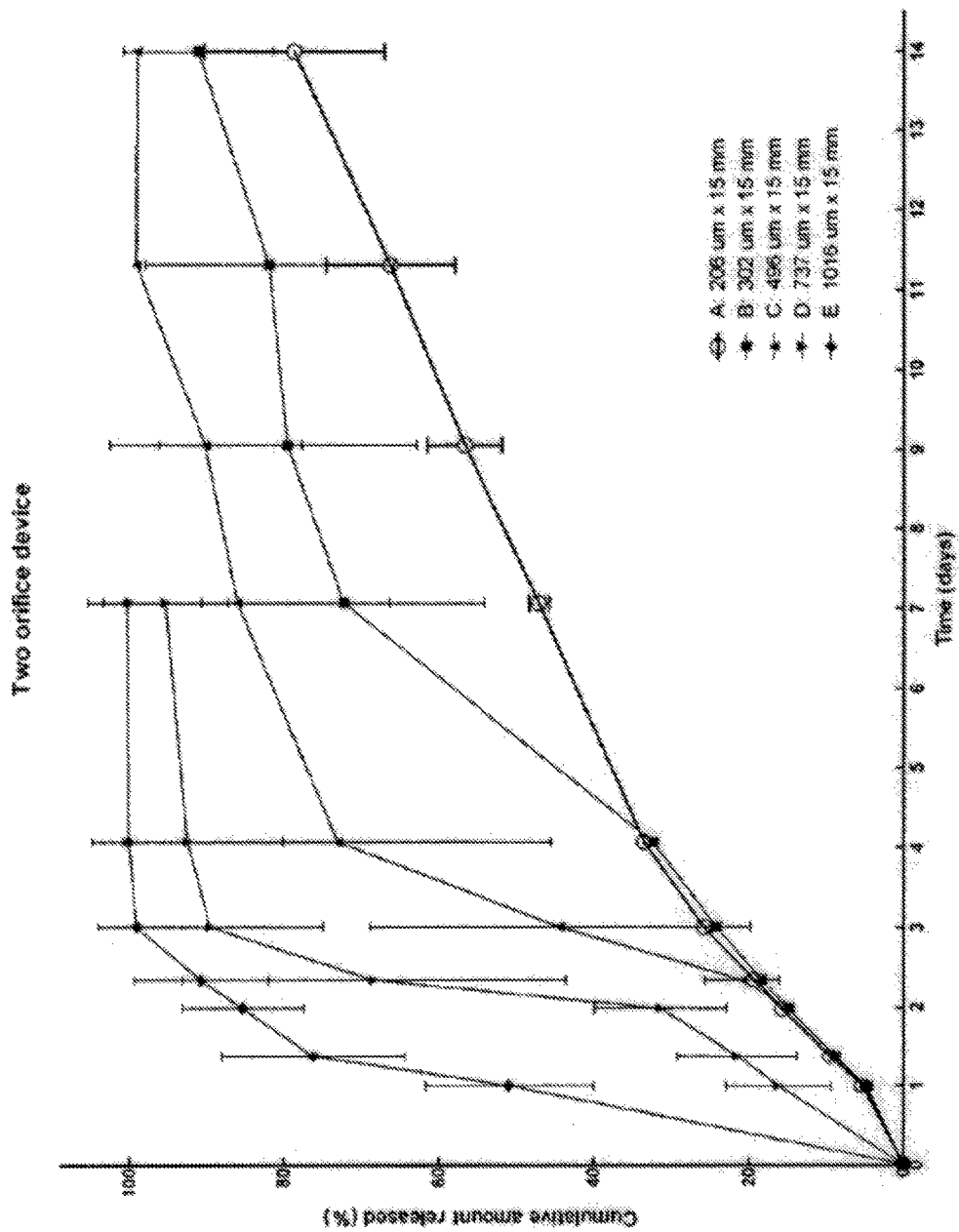
FIG. 11 is a graph of cumulative amount of drug released in vitro from a two-orifice system over time for a number of orifice dimensions, according to various embodiments.
Figure 12:
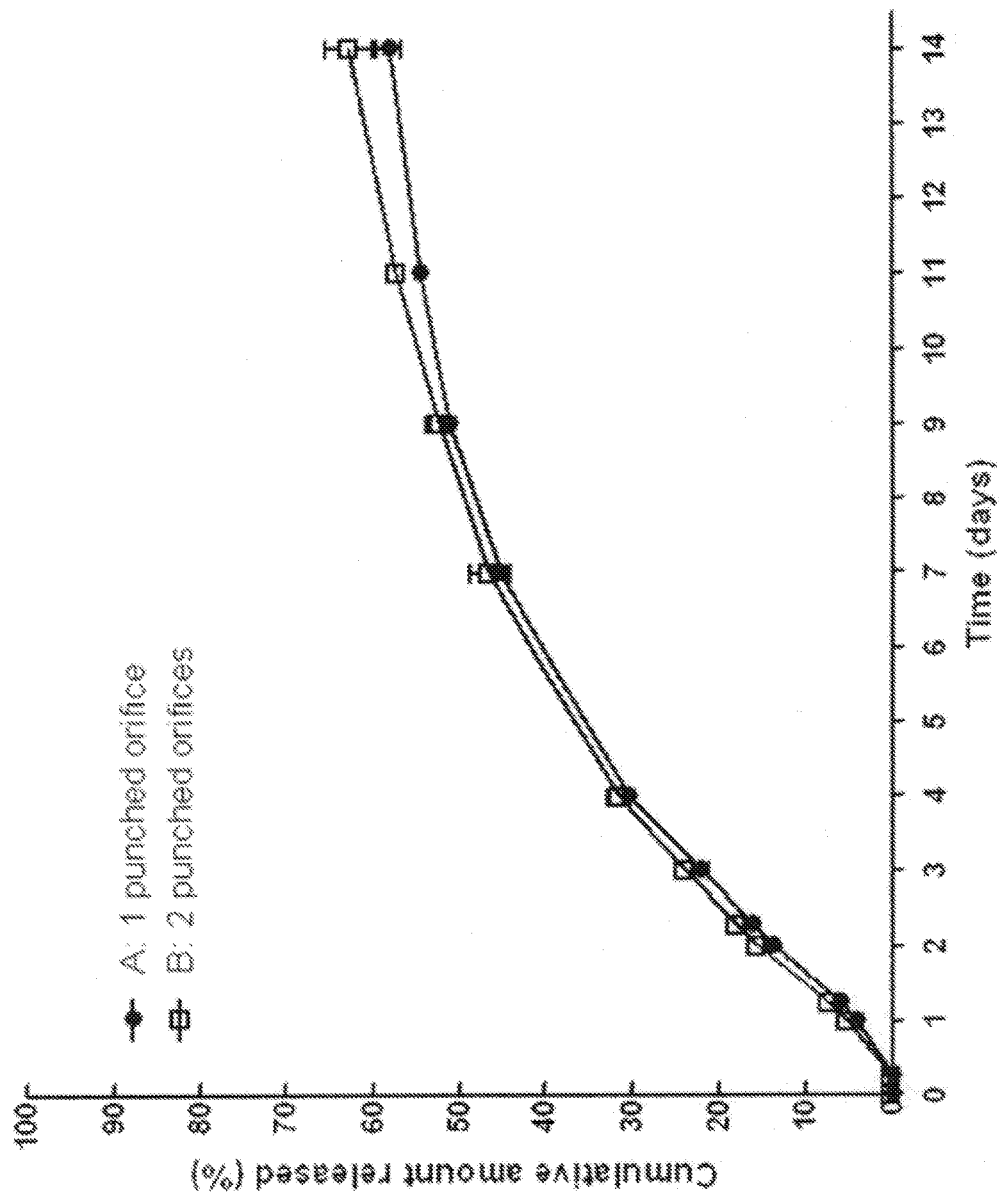
FIG. 12 is a graph of cumulative amount of drug released for a single-punched-orifice embodiment and a two-punched-orifices embodiment in certain examples.
Figure 13:
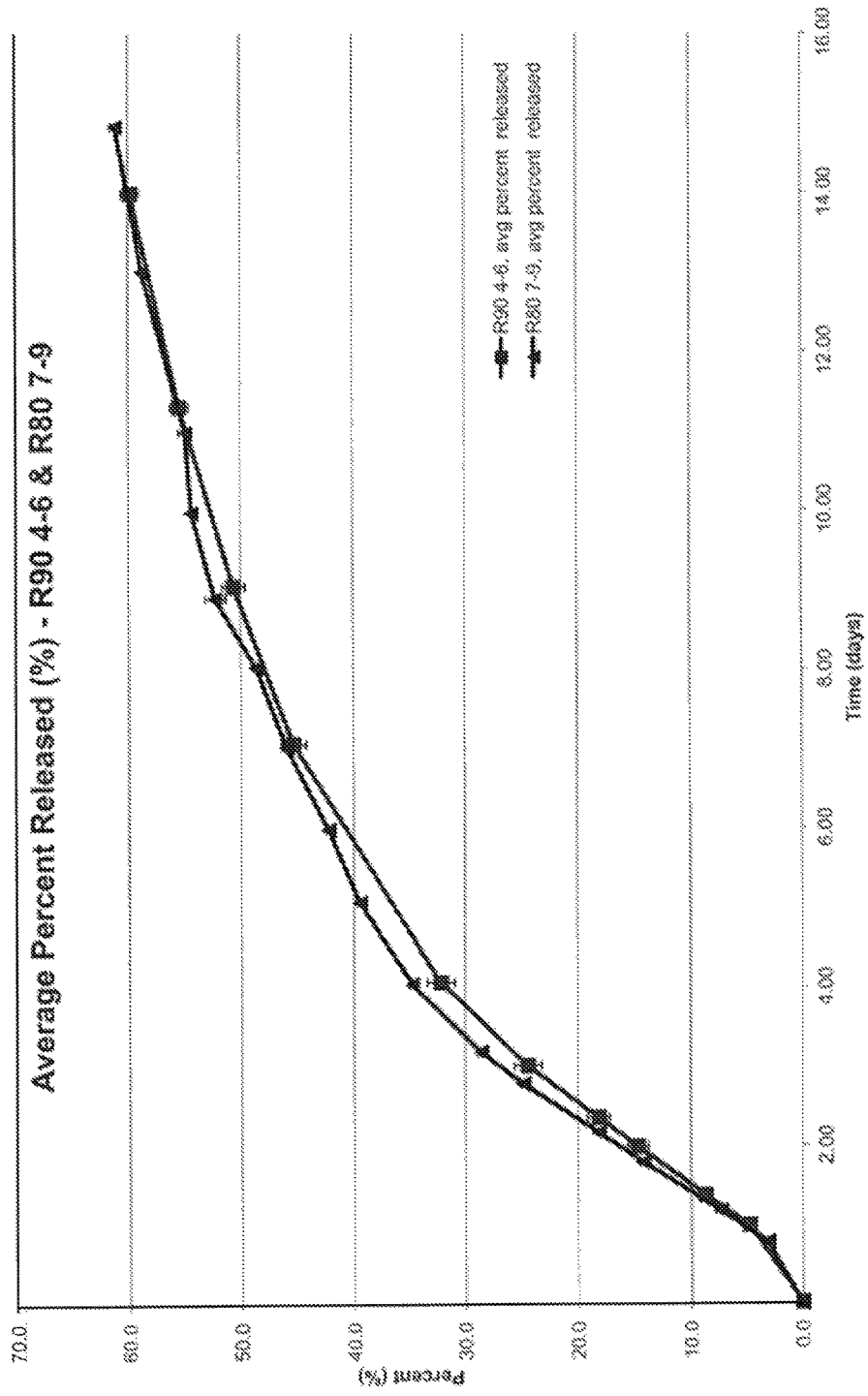
FIGS. 13-16 are graphs of percentage of drug released in vitro over time, according to various embodiments.
Figure 14:
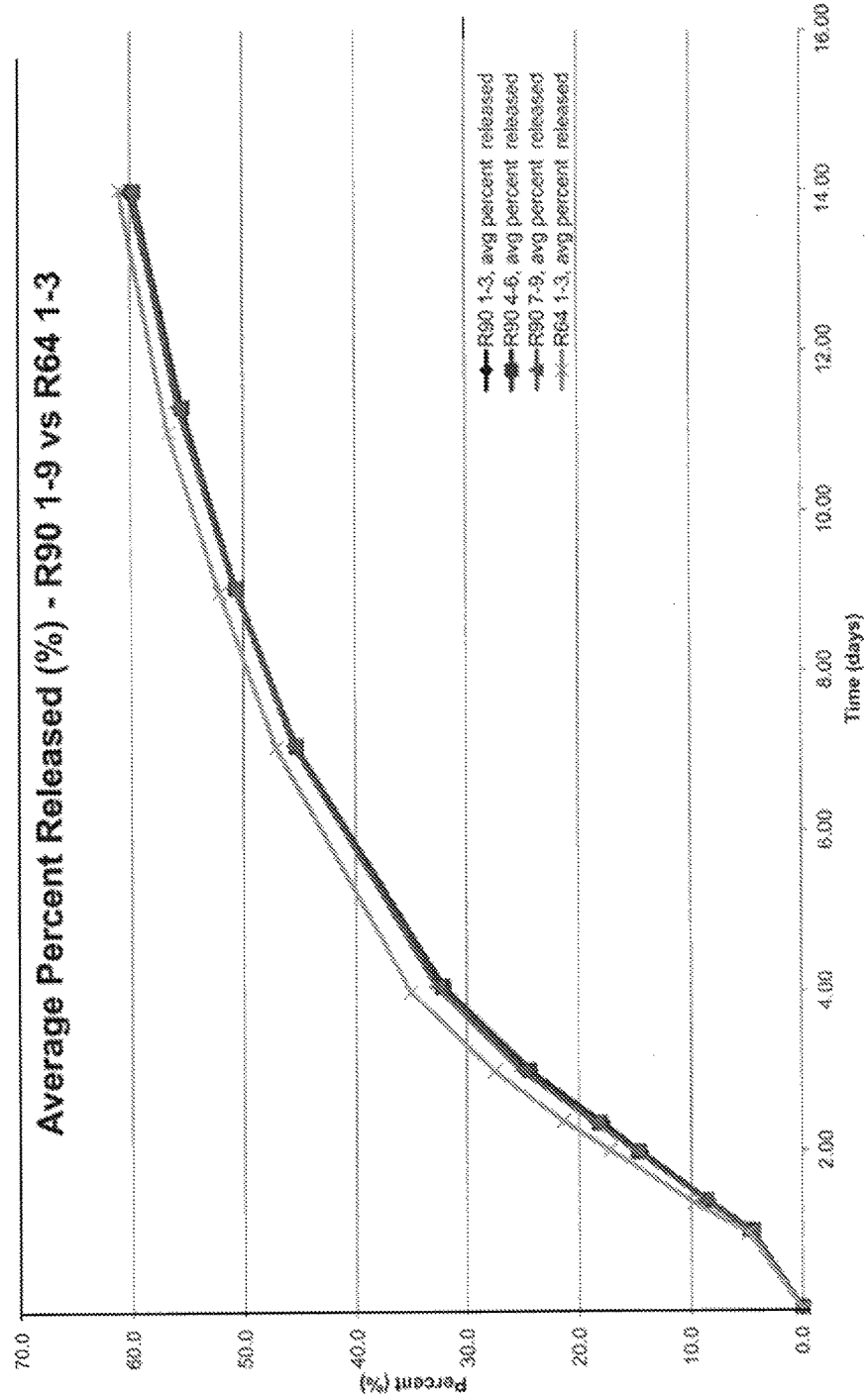
Figure 15:
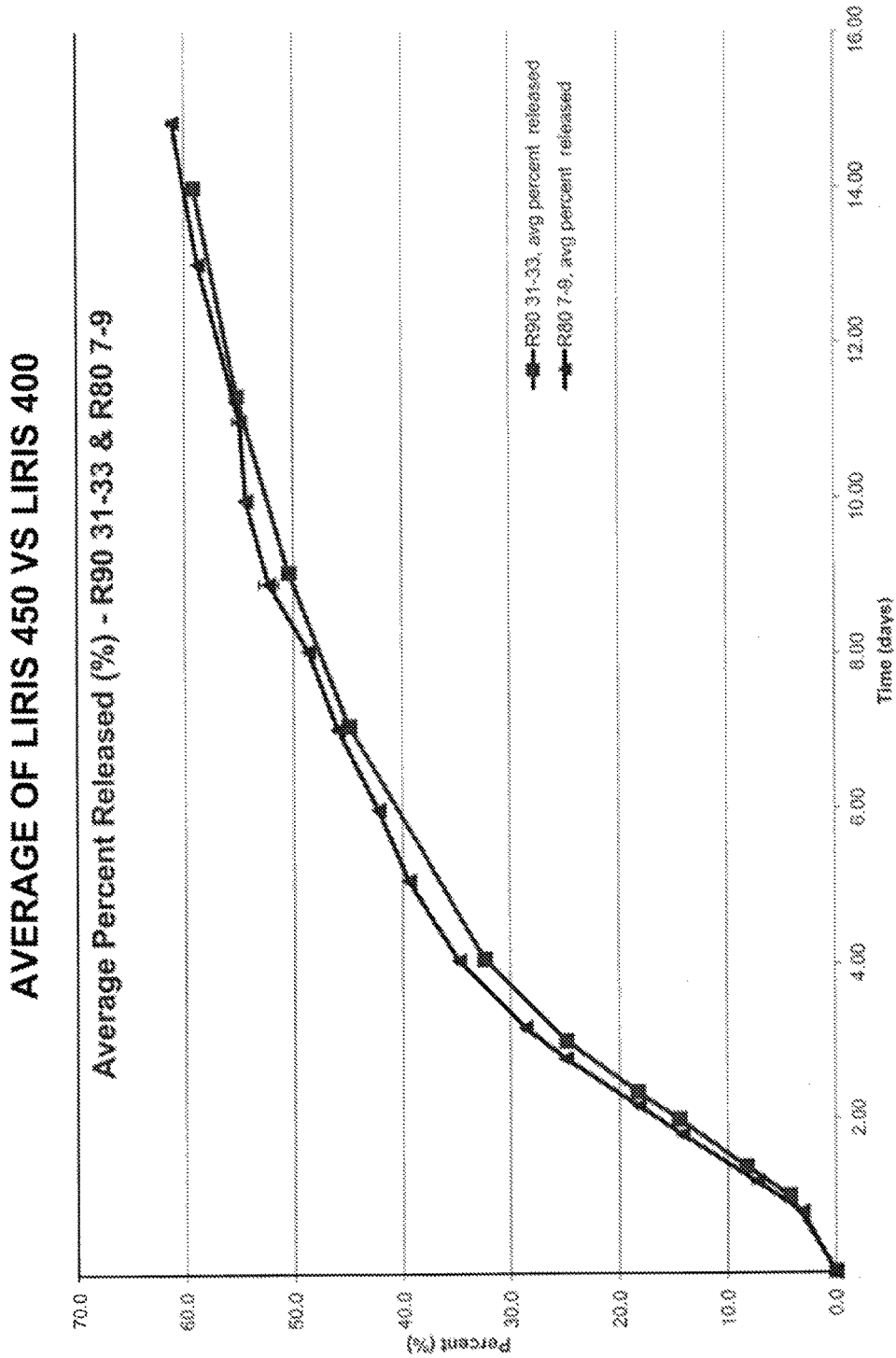
Figure 16:
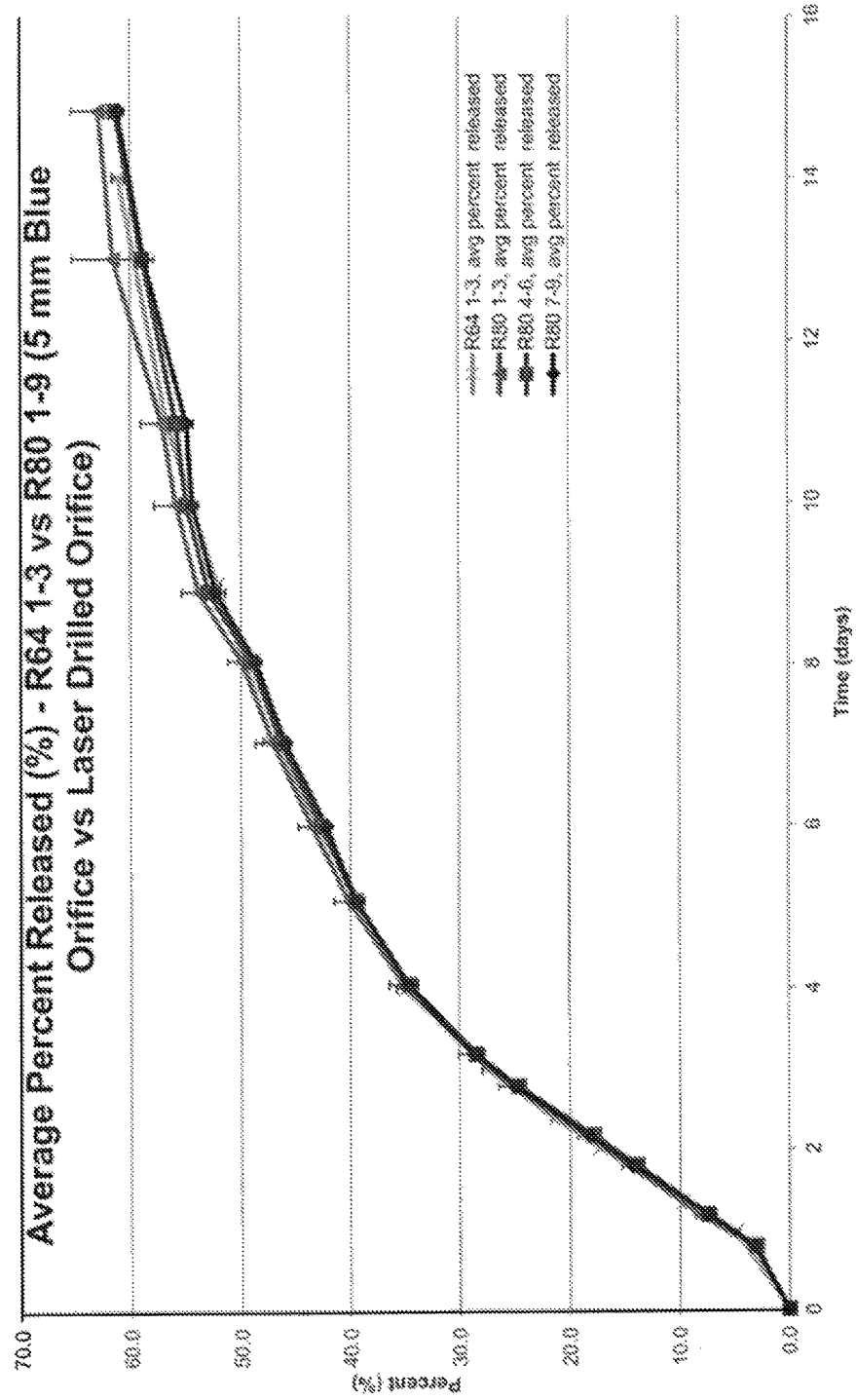

Each device was then placed in a jar containing aqueous liquid and samples of the liquid were tested for lidocaine periodically over 14 days to determine the cumulative amount of the drug released. The device structures are shown in FIGS. 9A-9C, and the corresponding results are shown in the graphs of FIGS. 10-12. For example, the device 900 in FIG. 9A includes an orifice 902 at one end and corresponds to lines A, B, C, D, E, and F in FIG. 10 and line A in FIG. 12. The device 910 in FIG. 9B includes an orifice 904 in the sidewall and corresponds to line G in FIG. 10. The device 912 in FIG. 9C includes an office 906, 908 at both ends and corresponds to lines A, B, C, D, and E in FIG. 11 and line B in FIG. 12. FIGS. 13-16 show that the percentage of drug released over time among the different devices with end apertures tracked closely with the laser drilled, sidewall based aperture. Accordingly, the study shows that it is feasible to replace with the tubing sidewall aperture with an aperture located at one or both ends of the tube.

Example 2: Production of Biodegradable End Plug with Orifice

Figure 18B:
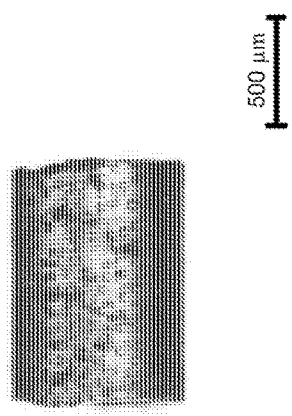
FIGS. 18A-18D shows various photographs of a PLGA end plug with an orifice according to one embodiment.
Figure 18D:
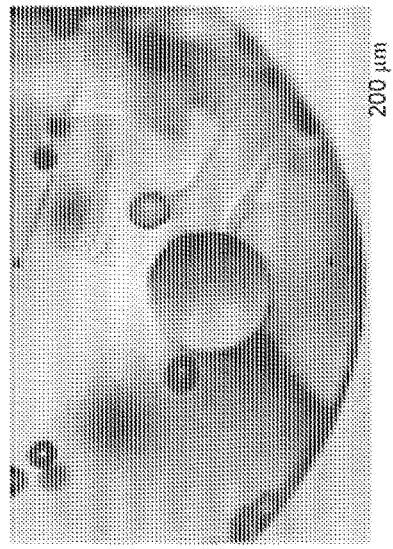
Figure 18A:
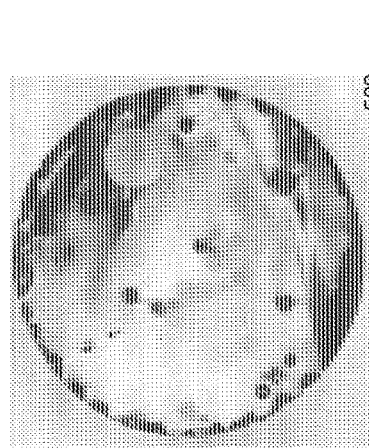
Figure 18C:
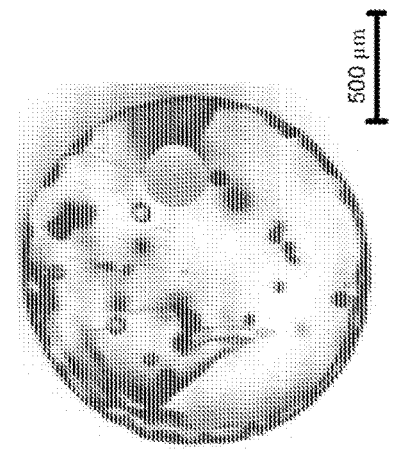

An end plug having a single orifice was made from PLGA (50:50) (Sigma-Aldrich, 719897, acid terminated, MW 7,000-17,000). The end plug was 1 mm in length, and the orifice was about 280 μm in diameter. It was made by melting PLGA and then casting it within a silicone tube while a wire having an outer diameter of about 280 μm was into the opening of the silicone tube and through the molten PLGA, while the PLGA cooled. Next, the wire was removed, and the PLGA plug was removed from the silicone tube. FIGS. 18A-1818D show photographs of the end plug produced.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An intravesical drug delivery device comprising:
   a device body comprising an elongated drug reservoir lumen and a retention frame lumen;
   a drug positioned in the drug reservoir lumen;
   a retention frame which comprises an elastic wire; and
   at least one end plug positioned at an end of the device body comprises an aperture through which the drug is released from the drug reservoir lumen,
   wherein the aperture has an initial diameter which is configured to release the drug in vivo predominately driven by osmosis, and, after a period within the bladder, the aperture has a second diameter which is greater than the initial diameter and with which release of the drug in vivo is predominately driven by diffusion.

2. The device of claim 1, wherein the aperture is defined by a bioerodible material.

3. The drug delivery device of claim 1, wherein the device body is formed of silicone and the at least one end plug is positioned within an end of the drug reservoir lumen.

4. The drug delivery device of claim 1, wherein the at least one end plug comprises poly (D, L-lactic-co-glycolic acid) (PLGA).

5. A drug delivery device for insertion into the bladder comprising:
   a device body comprising an elongated drug reservoir lumen;
   a drug positioned in the drug reservoir lumen; and
   at least one end plug positioned at an end of the device body, the end plug comprising an aperture therethrough,
   wherein the drug delivery device is configured to release the drug from the drug reservoir lumen through the aperture,
   wherein the aperture is defined and directly bounded by a bioerodible material configured to degrade in vivo such that a diameter of the aperture increases over time in vivo and/or such that a length of the end plug defining the aperture decreases over time in vivo.

6. The drug delivery device of claim 5, wherein the end plug is at least partially inserted into an end of the drug reservoir lumen.

7. The drug delivery device of claim 6, wherein the end plug has an outer diameter that is slightly larger than an inner diameter of the drug reservoir lumen.

8. The drug delivery device of claim 6, wherein the end plug has an outer diameter that is the same as or slightly smaller than an inner diameter of the drug reservoir lumen.

9. The drug delivery device of claim 6, wherein the end plug is secured within the drug reservoir lumen by an adhesive.

10. The drug delivery device of claim 9, wherein the end plug comprises a channel configured to receive the adhesive.

11. The drug delivery device of claim 6, further comprising a clamp positioned about the drug reservoir lumen and configured to secure the end plug within the drug reservoir lumen.

12. The drug delivery device of claim 6, wherein the end plug comprises one or more ribs disposed about an outer diameter of the end plug, the one or more ribs comprising a slightly larger outer diameter than an inner diameter of the drug reservoir lumen.

13. The drug delivery device of claim 5, wherein the end plug comprises a cavity configured to receive an end portion of a retention frame.

14. The drug delivery device of claim 5, wherein the bioerodible material comprises a biodegradable polymer.

15. A drug delivery device comprising:
a device body comprising an elongated drug reservoir lumen;
a drug positioned in the drug reservoir lumen; and
at least one end plug positioned at an end of the device body, the end plug comprising an aperture therethrough, the aperture having an opening extending through the at least one end plug and being in fluid communication with the drug reservoir lumen,
wherein the drug delivery device is configured to release the drug from the drug reservoir lumen through the aperture and the aperture is defined by a bioerodible material configured to degrade in vivo such that the opening of the aperture effective for drug release increases as the drug is released.

16. The device of claim 15, wherein the at least one end plug comprises:
an outer body portion having a first end, a second end, and a sidewall extending between the first and second ends;
a core portion extending through the outer body portion between the first and second ends; and
the aperture extending through the core portion between the first and second ends,
wherein the core portion, or an annular element disposed between the core portion and the outer body portion, is formed of a bioerodible material,
wherein the aperture of the at least one end plug is configured to change in at least one of length and diameter as the core portion degrades.

17. The device of claim 16, wherein the bioerodible material comprises PLA, PGA, PLGA, polyanhydrides, or another biodegradable polymer.

18. The device of claim 16, wherein the outer body portion is formed of a non-bioerodible polymer.

19. A method of administering a drug to a patient, comprising:
inserting into the patient the drug delivery device of claim 15; and
permitting the drug to be released from the inserted device through the aperture.

20. The method of claim 19, wherein the device is inserted into the patient's bladder.

21. The method of claim 20, wherein the aperture has an initial diameter with which release of the drug in vivo is predominately driven by osmosis, and, after a period within the bladder, has a second diameter which is greater than the initial diameter and with which release of the drug in vivo is predominately driven by diffusion.

22. A drug delivery device comprising:
a device body comprising an elongated drug reservoir lumen;
a drug positioned in the drug reservoir lumen; and
an end plug positioned at an end of the device body, wherein the end plug comprises (i) an outer body portion having a first end, a second end, and a sidewall extending between the first and second ends; (ii) a core portion extending through the outer body portion between the first and second ends; and (iii) an aperture extending through the core portion between the first and second ends,
wherein the core portion, or an annular element disposed between the core portion and the outer body portion, is formed of a bioerodible material which defines the aperture, the bioerodible material being configured to degrade in vivo such that the aperture is configured to change in at least one of length and diameter as the core portion degrades, whereby an opening of the aperture effective for drug release increases as the drug is released from the drug reservoir lumen through the aperture, and
wherein the outer body portion is formed of a bioerodible polymer having a slower rate of degradation than the bioerodible material forming the core portion.

* * * * *